US012564550B2

(12) United States Patent
Khaiat et al.

(10) Patent No.: US 12,564,550 B2
(45) Date of Patent: *Mar. 3, 2026

(54) ANTI-DANDRUFF COMPOSITION

(71) Applicant: Mane Kancor Ingredients Private Limited, Andheri (East) Mumbai (IN)

(72) Inventors: Alain Victor Khaiat, Singapore (SG); Sasheendran Vijayan, Kerala (IN); Shaju Asokan Vaikkathukattil, Kerala (IN); Prakash Kumar Unnikrishnan, Kerala (IN); Prasobh Sivaprasad, Kerala (IN)

(73) Assignee: Mane Kancor Ingredients Private Limited, Andheri (East) Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/496,388

(22) Filed: Oct. 27, 2023

(65) Prior Publication Data

US 2024/0050351 A1     Feb. 15, 2024

Related U.S. Application Data

(63) Continuation of application No. 17/053,705, filed as application No. PCT/IB2019/000370 on May 16, 2019, now Pat. No. 11,857,661.

(30) Foreign Application Priority Data

May 18, 2018     (IN) ............................. 201821018779

(51) Int. Cl.
| | |
|---|---|
| *A61K 8/9789* | (2017.01) |
| *A61K 8/31* | (2006.01) |
| *A61K 8/34* | (2006.01) |
| *A61K 8/35* | (2006.01) |
| *A61K 8/37* | (2006.01) |
| *A61K 8/49* | (2006.01) |
| *A61K 8/92* | (2006.01) |
| *A61K 31/015* | (2006.01) |
| *A61K 31/045* | (2006.01) |
| *A61K 31/05* | (2006.01) |
| *A61K 31/122* | (2006.01) |
| *A61K 31/215* | (2006.01) |
| *A61K 31/352* | (2006.01) |
| *A61K 36/534* | (2006.01) |
| *A61Q 5/00* | (2006.01) |
| *A61Q 5/02* | (2006.01) |
| *A61Q 17/00* | (2006.01) |

(52) U.S. Cl.
CPC .............. *A61K 8/9789* (2017.08); *A61K 8/31* (2013.01); *A61K 8/34* (2013.01); *A61K 8/347* (2013.01); *A61K 8/35* (2013.01); *A61K 8/37* (2013.01); *A61K 8/4973* (2013.01); *A61K 8/498* (2013.01); *A61K 8/922* (2013.01); *A61K 31/015* (2013.01); *A61K 31/045* (2013.01); *A61K 31/05* (2013.01); *A61K 31/122* (2013.01); *A61K 31/215* (2013.01); *A61K 31/352* (2013.01); *A61K 36/534* (2013.01); *A61Q 5/006* (2013.01); *A61Q 5/02* (2013.01); *A61Q 17/005* (2013.01); *A61K 2236/331* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 11,020,332 B2 | 6/2021 | Lerebour et al. | |
| 11,857,661 B2 * | 1/2024 | Khaiat | A61K 31/35 |
| 2003/0228272 A1 * | 12/2003 | Amjad | A61Q 5/12 |
| | | | 424/70.28 |
| 2014/0370136 A1 * | 12/2014 | Koo | A61Q 5/02 |
| | | | 424/777 |
| 2015/0086498 A1 | 3/2015 | Lerebour et al. | |

OTHER PUBLICATIONS

Wikipedia webpage "Tea tree oil" obtained from the website https://en.wikipedia.org/wiki/Tea_tree_oil (date unknown).*
Office Acton dated Sep. 4, 2024 in European Application 19 728 112.4.
Database GNPD [Online] MINTEL; Dec. 31, 2009, anonymous: "Ella Herbal Hair Oil", XP093200195, Database accession No. 1242180.
Moccia, et al, "Ellagic Acid Recovery by Solid State Fermentation of Pomegranate Wastes by Aspergillus niger and *Saccharomyces cerevisiae*: A Comparison", 2019, vol. 24, Molecules.
Sepulveda, et al, "Submerged culture for production of ellagic acid from pomegranate husk by Aspergillus niger GH1", Jul. 2014, pp. 27-35, vol. 26, No. 2, Micologia Aplicada International.
Caaballero, et al, "Biodegradation of Punicalagin into Ellagic Acid by Selected Probiotic Bacteria: A Study of the Underlying Mechanisms by MS-Based Proteomics", 2022, pp. 16273-16285, vol. 70, J. Agric. Food Chem.

* cited by examiner

*Primary Examiner* — Sin J Lee
(74) *Attorney, Agent, or Firm* — B. Aaron Schulman, Esq.; Stites & Harbison, PLLC

(57) ABSTRACT

Described herein is an anti-dandruff composition including at least two anti-dandruff actives selected from a punicalagin composition; a first monoterpenoid composition, or a second monoterpenoid composition; and a dermatologically-acceptable carrier. The two or more anti-dandruff actives are present in the anti-dandruff composition in an effective amount to treat or prevent dandruff caused by the proliferation of *Malassezia furfur*.

12 Claims, No Drawings

ANTI-DANDRUFF COMPOSITION

CROSS-REFERENCE TO RELATED APPLICATIONS

This application is a continuation application of U.S. patent application Ser. No. 17/053,705, having a filing date of Nov. 6, 2020, which is a US national phase application under 35 USC § 371 of International application No. PCT/IB2019/000370, filed May 16, 2019, which claims priority to Indian Patent Application No. 201821018779, filed May 18, 2018, the contents of all of said applications being hereby incorporated by reference in their entirety.

FIELD OF THE INVENTION

The present invention relates to antimicrobial compositions comprising naturally-derived anti-dandruff active materials, and more particularly to an anti-dandruff composition comprising a combination of a punicalagin composition and select monoterpenoid essential oils, the combinations of which are effective to inhibit *Malassezia furfur* and treat dandruff.

BACKGROUND OF THE INVENTION

Dandruff corresponds to excessive and visible desquamation of the scalp resulting from the excessively rapid multiplication of the epidermal cells and from their abnormal maturation. A variety of factors can induce this condition, such as excessive hair treatments, extreme climatic conditions, nervousness, diet, fatigue, or pollution. However, dandruff conditions most commonly arise from a disorder of the microflora of the scalp and more particularly from the excessive colonization by a fungus that belongs to the family of the yeasts of the genus *Malassezia*, which is naturally present on the scalp.

Dandruff, which affects up to 50% of the world's population and affects both men and women, generally has a negative psychosocial impact. Dandruff is disagreeable aesthetically (due to the visible presence of dead skin flakes) and because of the personal discomfort felt by the individual (in particular itching). Accordingly, affected persons confronted with this problem to variable degrees wish to be rid of it efficiently and permanently.

Many anti-dandruff treatments have been developed with the main objective of eradicating *Malassezia* yeasts from the scalp. Thus, the activity of the anti-dandruff active agents of today, such as zinc pyrithione, piroctone olamine, climbazole, ketoconazole, or selenium di-sulfide, are based mainly on their fungicidal property. Recently, other formulations using nature-based alternatives have been described, such as an anti-dandruff composition based on ellagic acid and at least one essential oil as described in WO2011/138450, or a hydrolysable tannin-enriched active substance derived from *Punica granatum* as described in FR2908045.

Despite the foregoing, there continues to be a need for new effective natural solutions toward treating dandruff.

SUMMARY OF THE INVENTION

The present invention is premised on the realization that various combinations of anti-dandruff actives, selected from a punicalagin composition, a first monoterpenoid composition comprising (or consisting essentially of) p-cymene; and a second monoterpenoid composition comprising (or consisting essentially of) menthol, are effective to inhibit *Malassezia furfur* and thereby treat dandruff.

Thus, in accordance with an embodiment of the present invention, an anti-dandruff composition is provided that comprises (or consists essentially of) a combination of at least two anti-dandruff actives selected from the group consisting of a punicalagin composition; a first monoterpenoid composition comprising (or consisting essentially of) p-cymene; and a second monoterpenoid composition comprising (or consisting essentially of) menthol; and a dermatologically-acceptable carrier. The anti-dandruff actives are present in the anti-dandruff composition in an effective amount to treat or prevent dandruff.

In accordance with another embodiment of the present invention, an anti-dandruff hair care composition is provided that is suitable for the treatment of dandruff against *Malassezia furfur*. The composition includes the anti-dandruff actives, a dermatologically-acceptable carrier, and a shampoo matrix comprising at least one detersive surfactant selected from the group consisting of an anionic surfactant, a nonionic surfactant, an amphoteric surfactant, or a combination thereof.

In accordance with yet another embodiment of the present invention, a method for treating dandruff conditions associated with the proliferation of yeasts of the *Malassezia* genus on a scalp of a subject is provided. The method comprises applying an effective amount of the anti-dandruff composition to the scalp of the subject, wherein the effective amount of the anti-dandruff composition inhibits the proliferation of the yeasts of the *Malassezia* genus on the scalp.

The objects and advantages of the present invention will be further appreciated in light of the following detailed description and examples.

DETAILED DESCRIPTION OF EMBODIMENTS OF THE INVENTION

The present invention relates to anti-dandruff compositions, and methods of using those compositions to treat or inhibit dandruff. The anti-dandruff compositions are useful for application to keratinous tissue or scalp surface and comprise an effective amount of a combination of anti-dandruff actives, and which inhibit, reduce, or eliminate dandruff symptoms arising from the proliferation of *Malassezia furfur*. The anti-dandruff compositions may be in a wide variety of product forms that include, but are not limited to, solutions, suspensions, lotions, creams, gels, ointments, sprays, aerosols, shampoos, hair conditioners, pastes, foams, powders, mousses, wipes, strips, patches, hydrogels, film-forming products, and the like. The compositional form may follow from the particular dermatologically-acceptable carrier chosen.

As used herein, the term "anti-dandruff composition" includes compositions that are applied to the hair and/or the skin underneath the hair, and comprise (or consist essentially of) at least one of various combinations of a punicalagin composition; a first monoterpenoid composition comprising (or consisting essentially of) p-cymene; and a second monoterpenoid composition comprising (or consisting essentially of) menthol; and a dermatologically-acceptable carrier, the combinations of which are effective to inhibit *Malassezia furfur* and treat dandruff.

The term "topical application," as used herein, means to apply or spread the compositions of the present invention onto the surface of the scalp from which mammalian hair grows.

The term "dermatologically-acceptable," as used herein, means that the compositions or components thereof so described are suitable for use in contact with mammalian keratinous or skin tissue without undue toxicity, incompatibility, instability, allergic response, and the like.

The term "anti-dandruff active", as used herein, refers to a single compound or a composition that possesses an ability to inhibit the proliferation of *Malassezia furfur*, when present in a medium in an effective amount.

The term "effective amount," as used herein, means an amount of a compound or composition sufficient to reduce or inhibit the proliferation of *Malassezia furfur*, reduce or inhibit the visible effects of dandruff caused by the proliferation of *Malassezia furfur*, or reduce or inhibit scalp pruritus, by a statistically significant amount.

The term "minimum inhibitory concentration," also abbreviated as "MIC," refers to the lowest concentration of the anti-dandruff active that will inhibit the growth of *Malassezia furfur* after incubation (at least 24 hours to 72 hours; 32.5° C.±2.5° C.) of a 1% agar solution mixed with an equal volume of an inoculated broth. Inhibition is defined as giving less than 20% growth compared to a control, as determined by spectrophotometric optical density (OD) reading at 620 nm, using the formula % of growth= $[(OD_{product}-OC_{absorbance-control})]/(OD_{positive\ growth-control})$.

Anti-Dandruff Composition

In accordance with embodiments of the present invention, the anti-dandruff composition comprises (or consists essentially of) an effective amount of a combination of at least two anti-dandruff actives selected from the group consisting of A) a punicalagin composition; B) a first monoterpenoid composition comprising (or consisting essentially of) p-cymene; and C) a second monoterpenoid composition comprising (or consisting essentially of) menthol; the combination of which is effective to inhibit *Malassezia furfur* and treat dandruff; and a dermatologically-acceptable carrier.

A. Punicalagin Composition

The term "punicalagin composition," as used herein, refers to a composition comprising at least 0.1 weight percent (wt %) of punicalagin A, punicalagin B, or a combination of the anomers. For example, the punicalagin content of the punicalagin composition may be, on a dry weight basis, 0.2 wt %, 1 wt %, 5 wt %, 10 wt %, 20 wt %, 30 wt %, 50 wt %, 75 wt %, or more, or within a range between any two of the foregoing. In one embodiment, the punicalagin content of the punicalagin composition is, on a dry weight basis, 30 wt % or more. Punicalagin may be synthetic or may be derived from a botanical such as *Punica granatum* (pomegranate), *Terminalia catappa* (Indian-almond), *Terminalia myriocarpa* (East Indian almond), or *Combretum molle* (velvet bushwillow). In accordance with an embodiment, the punicalagin composition is derived from *Punica granatum*. For example, the punicalagin composition may be a pomegranate extract.

The term "pomegranate extract," as used herein, refers to a product obtained by an extractive process from pomegranate (*Punica granatum*). Pomegranates are rich in antioxidants, with that activity being primarily attributable to polyphenols such as punicalagin A and B, punicalin, ellagic acid, gallic acid, etc. and often expressed in terms of gallic acid equivalents (GAE). While also present in pomegranate bark, seed, pulp, juice, and pericarp, the majority of the punicalagins and other ellagitannins, such as punicalin, is found in the skin (also called the rind or peel) of the fruit. Thus, in accordance with an embodiment, the solid pomegranate material may be a dried pomegranate rind or peel, which has been ground or flaked to reduce particle size thereby increasing the available surface area for extraction. In another embodiment, fresh pomegranate peels are utilized.

Accordingly, in one embodiment, the pomegranate extract is a composition produced by a general method comprising the steps of: (a) contacting a solid pomegranate material with an aqueous extraction liquid (e.g., water or a mixture of a water-miscible organic solvent and water); and (b) filtering or centrifuging the resulting mixture to separate the extracted pomegranate solids from the aqueous fraction. The process may be repeated multiple times, and the combined aqueous fractions concentrated to remove the water-miscible organic solvent, water, and/or any other volatiles. The pomegranate extract can be standardized by dilution to a desired extent with an appropriate diluent.

The selection of a suitable water-miscible organic solvent for the aqueous extraction liquid is not particularly limited, so long as the desired punicalagins are soluble therein. Non-limiting examples include methanol, ethanol, propanol, butanol, acetone, propylene glycol, butylene glycol, dimethylformamide, dimethyl sulfoxide, or combinations thereof. The volume ratio between the water-miscible organic solvent and water can vary between about 9:1 to about 1:9, for example about 7:1, about 3:1, about 2:1, about 1:1, about 1:2, about 1:3, about 1:7, or in a range between any two of the foregoing. In an embodiment, the aqueous extraction liquid is water. In another embodiment, the aqueous extraction liquid is an aqueous alcoholic solution. For example, the aqueous extraction liquid may be water, or it may comprise a 1:1 mixture of ethanol and water (i.e., 50% aqueous ethanol).

The ratio of the mass of the extracting solution to the mass of pomegranate solids can vary depending on a variety of factors, such as vessel size, extraction efficiency, and the like. A suitable range of ratios includes, but is not limited to, about 1:1 to about 25:1, such as 2:1, 4:1, 6:1, 8:1, 10:1, 15:1, 20:1, or in a range between any two of the foregoing.

The pomegranate extraction may be performed at a variety of pressures or temperatures. For example, the extraction can be conducted at ambient pressure and/or room temperature, or the extraction may be performed under pressure and/or at an elevated temperature. In one embodiment, the pomegranate extraction is performed near atmospheric pressure, and at a temperature within in a range from about 40° C. to about 100° C., such as about 50° C., about 60° C., about 70° C., about 80° C., or in a range between any two of the foregoing.

Evaporation (e.g., lyophilization) of the extracting liquids provides a solid, pomegranate extract that is enriched in punicalagin. In accordance with an embodiment, the punicalagin composition comprises at least 0.1 wt % of the punicalagin anomers, on a dry weight basis of the extract. In accordance with another embodiment, the punicalagin composition comprises less than 5 wt % of ellagic acid, on a dry weight basis of the extract. In accordance with another embodiment, the punicalagin composition comprises a polyphenol content of at least 30 GAE (by Folin-Ciocalteu Method), on a dry weight basis of the extract. If desired, the punicalagin composition may be standardized to a target polyphenol content with an acceptable diluent. A non-limiting example of a suitable diluent is a polyol, such as glycerol. In one example, the punicalagin composition is diluted with glycerol to provide a standardized solution having a phenolic content of 12% GAE.

In accordance with another embodiment, the pomegranate extract may be processed to further enrich the punicalagin concentration. For example, the pomegranate extract may be purified using chromatographic, precipitation, complexation, or other standard techniques to increase the punicalagin content of the extract. For example, the punicalagin content of the pomegranate extract may be, on a dry weight basis, 0.2 wt %, 1 wt %, 5 wt %, 10 wt %, 20 wt %, 30 wt %, 50 wt %, 75 wt %, or more, or within a range between any two of the foregoing. In one embodiment, the punicalagin content of the punicalagin composition is 30 wt % or more, on a dry weight basis of the extract.

In one example, extraction of dried, flaked pomegranate rind (having a polyphenolic content of about 20-25 wt % as determined by Folin-Ciocalteu Method) is performed six times with 50% aqueous ethanol (liquid to solid mass ratio of about 4:1) at 60° C. to 70° C. The combined liquids were filtered, and then evaporated to near dryness to provide a solid material having a phenolic content of approximately 40-45% GAE. Analysis of the crude extract using High Performance Liquid Chromatography-Quadrupole Time of Flight Liquid (HPLC-QTOF) confirmed the presence of gallic acid, punicalagins A and B, punicalin, ellagic acid hexoside, ellagic acid pentoside, ellagic acid deoxyhexoside, ellagic acid, and galloyl HHDP hexoside. Quantification by HPLC revealed that ellagic acid was present in less than 5 wt %. The ellagic acid content may be further reduced using standard techniques, such as selective solvent treatments or column chromatography, to a level of 1 wt % or less, based on total weight of the punicalagin composition, where weight percentage is on a dry weight basis.

In vitro Inhibition testing of the pomegranate extract against *Malassezia furfur*, in accordance with the classic broth dilution protocol, revealed that the pomegranate extract possessed a minimum inhibition concentration (MIC) value of ≤0.1% against *Malassezia furfur* CIP 1634.84. Inhibition testing on a substantially pure sample of the punicalagin anomers (A:B, 1:2; 93 wt % pure; part No. 00016983, Chromadex, Inc., Irvice, CA), yielded a MIC value of 0.05% against *Malassezia furfur* CBS 1878. In comparison, ellagic acid (>95 wt %, prod. No. E2250, Sigma-Aldrich, St. Louis, MO) demonstrated a MIC value of 0.5% against *Malassezia furfur* CBS 1878.

In another embodiment, fresh peels are separated from the arils of whole pomegranates, and the peels, which may be subjected to size reduction, are mixed with water. The aqueous portions are collected and the solid residue pressed to expel residual aqueous fluid. This process may be repeated three or more times. The combined aqueous portions are centrifuged to remove suspended solids, and the aqueous portions passed through a packed column containing DIAION™ HP20 resin (Mitsubishi Chemical, Japan) to adsorb the polyphenols. Elution with 50% aqueous ethanol provided fractions rich in punicalagins, which were concentrated and spray dried to provide a solid pomegranate extract with a phenolic content of 70-75% GAE, with approximately 30 wt % punicalagins. A standardized solution was prepared by dilution with glycerol to a phenolic content of 12% GAE. In vitro inhibition testing of this standardized solution against *Malassezia furfur* CBS 1878, in accordance with the classic broth dilution protocol, revealed a minimum inhibition concentration (MIC) value of ≤0.05%. Thus, it was observed that increasing the punicalagin content of the pomegranate extract further reduces its MIC value against *Malassezia furfur*.

B. First Monoterpenoid Composition

The term "first monoterpenoid composition," as used herein, refers to a composition comprising (or consisting essentially of) para-cymene. In an embodiment, the first monoterpenoid composition comprises (or consists essentially of) para-cymene and thymol. In another embodiment, the first monoterpenoid composition further comprises (or consists essentially of) para-cymene and gamma-terpinene. In yet another embodiment, the first monoterpenoid composition comprises (or consists essentially of) para-cymene, thymol, and gamma-terpinene. In an embodiment, the para-cymene content of the first monoterpenoid composition is at least 20 wt %.

In an embodiment, the first monoterpenoid composition comprises 20-60 wt % gamma-terpinene, 20-60 wt % para-cymene, and 20-60 wt % thymol. In another embodiment, the combined masses of the gamma-terpinene, para-cymene, and thymol constitute at least 80 wt % of the first monoterpenoid composition. In yet another embodiment, the first monoterpenoid composition comprises gamma-terpinene, para-cymene, and thymol in a mass ratio of about 2:1:1, respectively.

In another embodiment, the first monoterpenoid composition is derived from an ajowan (*Trachyspermum ammi* syn *Carum copticum*) essential oil. As used herein, the term "essential oil," refers to a concentrated hydrophobic liquid containing volatile aroma compounds from a botanical (plant) source, which may include the plant roots, leaves, stems, fruits, seeds, rinds, etc. Generally speaking, selection of the technique for obtaining an essential oil depends mainly on the starting material, i.e., the plant's original state, its characteristics, and the nature of its aroma compounds. The technique conditions the characteristics of the essential oil, in particular viscosity, color, solubility, volatility, and richness or poorness in certain constituents. Common techniques for obtaining essential oils include solvent or supercritical fluid extractions, cold pressing, or distillation, which can be carried out under a variety of conditions, e.g., dry distillation, hydrodistillation, steam distillation, etc.

In accordance with an embodiment, the ajowan essential oil is obtained by steam distillation. Generally, steam distillation corresponds to the vaporization, in the presence of steam, of a substance that is not very miscible with water. The starting material together with water brought to boiling point (hydrodistillation), or with steam in a still (dry distillation). The steam entrains the essential oil vapor, which is condensed and recovered as a separate liquid phase from the water.

In an embodiment, the ajowan essential oil is obtained by a typical steam distillation process. Ajowan seeds are ground and charged in an extraction vessel. The ground ajowan seeds are moistened first before applying direct steam. A typical steam distillation of ground ajowan seeds takes 10 hours or more until the desired recovery oil content is reached, and provides an oil yield of approximately 2 to 2.5 wt %, based on the weight of the ground seed starting material. Based on GC/MS analysis, the ajowan seed steam distilled essential oil includes the following listing of major components gamma-terpinene, thymol, and para-cymene.

In vitro Inhibition testing of the ajowan essential oil against *Malassezia furfur*, in accordance with the classic broth dilution protocol, revealed that the ajowan essential oil possessed a minimum inhibition concentration (MIC) value of 0.5% and 1.0% against *Malassezia furfur* CIP 1634.84 and *Malassezia furfur* CBS 1878, respectively. In vitro inhibition testing of the major components of ajowan essential oil (i.e., gamma-terpinene, para-cymene, and thymol) revealed that gamma-terpinene, para-cymene, and thymol possessed MIC values of >1%, 0.5%, and 0.05%, respectively, against *Malassezia furfur* CBS 1878.

C. Second Monoterpenoid Composition

The term "second monoterpenoid composition," as used herein, refers to a composition comprising (or consisting essentially of) menthol. In an embodiment, the second monoterpenoid composition comprises (or consists essentially of) menthol, menthone, isomenthone, menthyl acetate, neomenthol, limonene, or combinations thereof (e.g. comprises—or consists essentially of—menthol, menthone, isomenthone, menthyl acetate, neomenthol and limonene). In another embodiment, the second monoterpenoid composition comprises 70-80 wt % menthol, 5-10 wt % menthone, 5-10 wt % isomenthone, 5-10 wt % menthyl acetate, 5-10 wt % neomenthol, and 1-5 wt % limonene. In yet another embodiment, the second monoterpenoid composition is derived from a corn mint (*Mentha arvensis*) essential oil. In a typical steam distillation of corn mint to produce an essential oil, semi-dried *Mentha arvensis* is charged to a steam distillation vessel, packed well, and steam slowly applied to distill out the oil. Depending on a variety of factors, a typical steam distillation process of corn mint may take between 5 and 7 hours, and provides an oil yield of approximately 1.4 to 1.6 wt %, based on the weight of the semi-dried corn mint starting material. Based on GC/MS analysis, the corn mint essential oil product includes the following listing of components menthol, menthone, isomenthone, menthyl acetate, neomenthol, and limonene.

In vitro Inhibition testing of the corn mint essential oil against *Malassezia furfur*, in accordance with the classic broth dilution protocol, revealed that the corn mint essential oil possessed a minimum inhibition concentration (MIC) value of 0.5% against *Malassezia furfur* CIP 1634.84, and a MIC value of 1% against *Malassezia furfur* CBS 1878.

As noted above, the anti-dandruff active portion of the anti-dandruff composition comprises (or consists essentially of) a combination of at least two of the three described anti-dandruff actives (i.e., the punicalagin composition, the first monoterpenoid composition, and the second monoterpenoid composition). The combinations are based on the additive or synergistic relationship between the individual anti-dandruff actives. Inhibition testing of the individual anti-dandruff actives to determine MIC levels followed the principles and general methods disclosed in C. Lens-Lisbonne, et al. "Methods for the evaluation of antibacterial activity of essential oils: applications to essences of thyme and cinnamon," J. Pharm. Belg., 1987, 42(5): 297-302; and C. Lisbonne "Evaluation of bacteriostatic activity of essential oils and their components," Doctoral Thesis, Pharmacy Faculty, Marseille, FR 1988. Interactions of bi-component mixtures (Fractional Inhibitory Concentration) were evaluated in accordance with the method described by J. L. Pons et al., "Evaluation of antimicrobial interactions between chlorhexidine, quaternary ammonium compounds, preservatives and excipients," J. Appl. Bacteriol., 1992, 73, 395-400, to assess their additive or synergistic effects.

In an embodiment, the punicalagin-containing pomegranate extract, the ajowan essential oil, and the corn mint essential oil, proved to inhibit *Malassezia furfur* in in vitro experiments at MIC values in a range from about 0.1% (w/v) to about 1.0% (w/v). Bi-component mixtures of the pomegranate extract (punicalagins content about 0.2 wt % on a dry weight basis) and the ajowan essential oil; and the ajowan essential oil and the corn mint essential oil demonstrated synergistic activities against *Malassezia furfur*, whereas the bi-component mixture of the pomegranate extract (punicalagins content about 0.2 wt % on a dry weight basis) and the corn mint essential oil demonstrated an additive relationship. However, the bi-component mixture of a pomegranate extract having a punicalagins content of about 30 wt % on a dry weight basis and the corn mint essential oil demonstrated synergistic activities against *Malassezia furfur*. Additional synergy testing of bi-component mixtures of the pomegranate extract having a punicalagins content of about 30 wt % on a dry weight basis with the major components of the ajowan essential oil (para-cymene, gamma-terpinene, and thymol) revealed that punicalagins and para-cymene demonstrated synergistic activities against *Malassezia furfur.*

Thus in accordance with an embodiment, the anti-dandruff composition comprises (or consists essentially of) a combination of the punicalagin composition and the second monoterpenoid composition, along with a dermatologically-acceptable carrier. In accordance with another embodiment, the anti-dandruff composition comprises (or consists essentially of) a combination of the punicalagin composition and the first monoterpenoid composition, along with a dermatologically-acceptable carrier. In accordance with yet another embodiment, the anti-dandruff composition comprises (or consists essentially of) a combination of the first and second monoterpenoid compositions, along with a dermatologically-acceptable carrier. And in accordance with yet another embodiment, the anti-dandruff composition comprises (or consists essentially of) a combination of the punicalagin composition, the first monoterpenoid composition, and the second monoterpenoid composition, along with a dermatologically-acceptable carrier.

When used as one of the active components, the punicalagin composition is present in the anti-dandruff composition in an amount between about 0.1 wt % and 10 wt %. For example, the punicalagin composition (e.g. pomegranate extract) may comprise 0.1 wt %, 0.2 wt %, 0.5 wt %, 0.75 wt %, 1.0 wt %, 2.0 wt %, 5.0 wt %, 7.5 wt %, 10 wt % of the anti-dandruff composition, or in a range between any two of the foregoing. When used as one of the active components, the first monoterpenoid composition is present in the anti-dandruff composition in an amount between about 0.1 wt % and 5 wt %. For example, the first monoterpenoid composition (e.g. ajowan essential oil) may comprise 0.1 wt %, 0.2 wt %, 0.5 wt %, 0.75 wt %, 1.0 wt %, 2.0 wt %, 5.0 wt % of the anti-dandruff composition, or in a range between any two of the foregoing. When used as one of the active components, the second monoterpenoid composition is present in the anti-dandruff composition in an amount between about 0.1 wt % and 10 wt %. For example, the second monoterpenoid composition (e.g. corn mint essential oil) may comprise 0.1 wt %, 0.2 wt %, 0.5 wt %, 0.75 wt %, 1.0 wt %, 2.0 wt %, 5.0 wt %, 7.5 wt %, 10 wt % of the anti-dandruff composition, or in a range between any two of the foregoing. Wt % is based on the weight of the entire anti-dandruff composition.

D. Dermatologically Acceptable Carrier

The anti-dandruff compositions of the present invention comprise a dermatologically-acceptable carrier (which may be referred to as "carrier") for the anti-dandruff actives composition. A suitable carrier is selected to yield a desired product form. Furthermore, the solubility or dispersibility of the components may dictate the form and character of the carrier. In one embodiment, the carrier is present at a level of from about 30 wt % to about 99 wt %, about 40 wt % to about 98 wt %, about 50 wt % to about 96 wt %, or, alternatively, from about 60 wt % to about 95 wt %, by weight of the composition. Wt % is based on the weight of the entire composition.

The carrier can be in a wide variety of forms. Non-limiting examples include simple solutions (e.g., aqueous, organic solvent, or oil based), emulsions, and solid forms (e.g., gels, sticks, flowable solids, or amorphous materials). In certain embodiments, the carrier is an aqueous carrier, which may comprise water or natural botanical juices, such as aloe vera water. In certain embodiments, the dermato-logically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

For emulsions, the aqueous phase comprises water, such as demineralized or distilled water, for example. Other acceptable carriers that may be used in the aqueous carrier include, but are not limited to alcohol or ether compounds, such as ethanol, glycerol, dipropylene glycol, propylene glycol, butylene glycol, 1,4-butanediol, 3-allyloxy-1,2-pro-panediol, dipropylene glycol n-butyl ether, 1,2-hexanediol, dimethyl isosorbide, 1,3-butanediol, 1,3-propanediol, 2,2'-thiodiethanol, and 1,6-hexanediol, or combinations thereof.

The anti-dandruff compositions may have a pH ranging from about 3.0 to about 10.5, which may be measured by taking a direct pH measurement using a standard hydrogen electrode of the composition at 25° C. Accordingly, the pH of the anti-dandruff composition may be within the range from about 6 to about 9, for example.

E. Optional Ingredients

The anti-dandruff compositions of the present invention may be prepared in typical anti-dandruff formulations. They may be in the form of solutions, dispersion, emulsions, powders, talcs, encapsulated, spheres, spongers, solid dos-age forms, foams, and other delivery mechanisms. The compositions of the embodiments of the present invention may be hair tonics, leave-on hair products such as condi-tioners, treatment, and styling products, rinse-off hair prod-ucts such as conditioners, shampoos, and treatment prod-ucts; and any other form that may be applied to the scalp.

Accordingly, the anti-dandruff compositions may also include other common hair ingredients. The CTFA Cosmetic Ingredient Handbook, Tenth Edition (published by the Cos-metic, Toiletry, and Fragrance Association, Inc. (now called The Personal Care Products Council), Washington, D.C.) (2004), describes a wide variety of nonlimiting materials that can be added to the composition herein. Examples of these ingredient classes include, but are not limited to: abrasives, absorbents, fragrances, pigments, colorings/colo-rants, essential oils, skin sensates, astringents, anti-acne agents, anti-caking agents, antifoaming agents, antimicro-bial agents, antioxidants, binders, biological additives, buff-ering agents, bulking agents, chelating agents, film formers, opacifying agents, pH adjusters, propellants, reducing agents, sequestrants, rheology modifiers, conditioning agents, emulsifiers, and surfactants In accordance with an embodiment, the anti-dandruff com-position may be formulated as a hair care composition, such as a shampoo, a hair conditioner, or a shampoo-conditioner combination, which further include one or more of the following ingredients 1) surfactants (anionic, amphoteric/zwitterionic, non-ionic), 2) conditioning agents, 3) emulsi-fiers, 4) opacifiers, 5) thickeners, and 6) buffers. Accord-ingly, in one embodiment, the anti-dandruff composition of the invention may be formulated as an anti-dandruff hair care composition, with a shampoo matrix comprising at least one detersive surfactant selected from the group consisting of an anionic surfactant, a nonionic surfactant, an ampho-teric surfactant, or a combination thereof.

1. Surfactants

The hair care composition of the present invention may include a detersive surfactant, which provides cleaning performance to the composition. The detersive surfactant in turn may comprise an anionic surfactant, an amphoteric/zwitterionic surfactant, a non-ionic, or mixtures thereof. Various examples and descriptions of detersive surfactants are set forth in U.S. Pat. No. 6,649,155; U.S. Patent Appli-cation Publication No. 2008/0317698; and U.S. Patent Application Publication No. 2008/0206355, which are incorporated herein by reference in their entirety.

The concentration of the detersive surfactant component in the hair care composition should be sufficient to provide the desired cleaning and lather performance, and generally ranges from about 2 wt % to about 50 wt %, from about 5 wt % to about 40 wt %, from about 8 wt % to about 35 wt %, or from about 10 wt % to about 30 wt %. Accordingly, the hair care composition may comprise a detersive surfac-tant in an amount of about 5 wt %, about 10 wt %, about 12 wt %, about 15 wt %, about 17 wt %, about 18 wt %, about 20 wt %, about 25 wt %, about 30 wt %, or in a range between any two of the foregoing, for example. Wt % is based on the weight of the entire composition.

Anionic surfactants suitable for use in the compositions are the alkyl and alkyl ether sulfates. Other suitable anionic surfactants are the water-soluble salts of organic, sulfuric acid reaction products. Still other suitable anionic surfac-tants are the reaction products of fatty acids esterified with isethionic acid and neutralized with sodium hydroxide. Other similar anionic surfactants are described in U.S. Pat. Nos. 2,486,921; 2,486,922; and 2,396,278, which are incor-porated herein by reference in their entirety.

Exemplary anionic surfactants for use in the hair care composition include ammonium lauryl sulfate, ammonium laureth sulfate, triethylamine lauryl sulfate, triethylamine laureth sulfate, triethanolamine lauryl sulfate, trietha-nolamine laureth sulfate, monoethanolamine lauryl sulfate, monoethanolamine laureth sulfate, diethanolamine lauryl sulfate, diethanolamine laureth sulfate, lauric monoglycer-ide sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, monoetha-nolamine cocoyl sulfate, sodium tridecyl benzene sulfonate, sodium dodecyl benzene sulfonate, sodium cocoyl isethio-nate and combinations thereof. In a further embodiment of the present invention, the anionic surfactant is sodium lauryl sulfate, sodium laureth sulfate, or a combination thereof.

Suitable amphoteric/zwitterionic surfactants for use in the hair care composition herein include those which are known for use in hair care or other personal care cleansing. Con-centrations of such surfactants range from about 0.5 wt % to about 20 wt %, and from about 1 wt % to about 10 wt %. Nonlimiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the hair care composition include those surfactants broadly described as derivatives of aliphatic secondary and tertiary amines in which the aliphatic radical can be straight or branched chain and wherein one of the aliphatic substituents contains from about 8 to about 18 carbon atoms, and at least one contains an anionic group such as carboxy, sulfonate, sulfate, phosphate, or phosphonate. Zwitterionic detersive surfactants suitable for use in the hair care composition include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Exemplary amphoteric and/or zwitterionic detersive surfactants for use in the present hair care composition include cocoamphoacetate, cocoamphodiacetate, lauroamphoacetate, lauroamphodiacetate, cocamidopropyl betaine, cocamidopropyl hydroxysultaine, and mixtures thereof.

Nonionic Surfactants: The shampoo compositions can comprise a nonionic surfactant. Nonionic surfactants include those compounds produced by condensation of alkylene oxide groups, hydrophilic in nature, with an organic hydrophobic compound, which may be aliphatic or alkyl aromatic in nature.

Nonlimiting examples of nonionic surfactants for use in the shampoo compositions include the following: (1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol; (2) those derived from the condensation of ethylene oxide with the product resulting from the reaction of propylene oxide and ethylene diamine products; (3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms; (4) long chain tertiary amine oxides of the formula $[R^1R^2R^3N{\rightarrow}O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals; (5) long chain tertiary phosphine oxides of the formula $[RR'R''P{\rightarrow}O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R'' are each alkyl or monohydroxyalkyl groups containing from about 1 to about 3 carbon atoms; (6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties; (7) alkyl polysaccharide (APS) surfactants (e.g. alkyl polyglycosides), examples of which are described in U.S. Pat. No. 4,565,647, which is incorporated herein by reference in its entirety, and which discloses APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); and (8) polyoxyethylene alkyl ethers, having a general formula $RO(CH_2CH_2)_nH)$, and polyethylene glycol (PEG) glyceryl fatty esters, having a general formula $R(O)OCH_2CH(OH)CH_2(OCH_2CH_2)_nOH)$, wherein n is from 1 to about 200, preferably from about 20 to about 100, and R is an alkyl having from about 8 to about 22 carbon atoms.

Certain nonionic surfactants can also function as foam stabilizers, viscosity control agents, or conditioning agents. Where included, the hair care composition may contain about 0.5 wt % to about 5.0 wt % nonionic surfactant, or about 0.75 wt % to about 2.0 wt %. Non limiting examples of other anionic, amphoteric/zwitterionic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

2. Conditioning Agent

In one embodiment of the present invention, the hair care compositions comprise one or more conditioning agents. Conditioning agents include materials that are used to give a particular conditioning benefit to hair and/or skin. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix. In an embodiment, one or more conditioning agents are present from about 0.01 wt % to about 10 wt %, from about 0.1 wt % to about 8 wt %, and from about 0.2 wt % to about 4 wt %, by weight of the entire composition.

3. Emulsifiers

A variety of anionic emulsifiers can be used in the shampoo composition of the present invention as described below. The anionic emulsifiers include, by way of illustrating and not limitation, water-soluble salts of alkyl sulfates, alkyl ether sulfates, alkyl isethionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, carboxymethylcellulose, cellulose sulfate and pectin, poly(styrene sulfonate), carrageenan, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxy-modified polyvinyl alcohol, sulfonic acid-modified polyvinyl alcohol and phosphoric acid-modified polyvinyl alcohol, phosphated or sulfated tristyrylphenol ethoxylates.

In addition, anionic emulsifiers that have acrylate functionality may also be used in the instant shampoo compositions. Anionic emulsifiers useful herein include, but aren't limited to: poly(meth)acrylic acid; copolymers of (meth) acrylic acids and its (meth)acrylates with C1-22 alkyl, C1-C8 alkyl, butyl; copolymers of (meth)acrylic acids and (meth)acrylamide; carboxyvinylpolymer; acrylate copolymers such as acrylate/C10-30 alkyl acrylate crosspolymer, acrylic acid/vinyl ester copolymer/acrylates/vinyl Isodecanoate crosspolymer, acrylates/palmeth-25 acrylate copolymer, acrylate/steareth-20 itaconate copolymer, and acrylate/ceteth-20 itaconate copolymer; polystyrene sulphonate, copolymers of methacrylic acid and acrylamidomethylpropane sulfonic acid, and copolymers of acrylic acid and acrylamidomethylpropane sulfonic acid; carboxymethycellulose; carboxy guar; copolymers of ethylene and maleic acid; and acrylate silicone polymer. In an embodiment, the emulsifier, when present, ranges from about 0.01 wt % to about 5 wt %, by weight of the entire anti-dandruff hair care composition, or from about 0.1 wt % to about 4 wt %, or from about 0.1 wt % to about 3 wt %. Wt % is based on the weight of the entire composition.

4. Opacifiers

Some formulations are often opacified by incorporating materials therein to achieve a cosmetically attractive pearl-like appearance, known as pearlescence. The opacifying or pearlescent materials include, but are not limited to, titanium dioxide coated mica, iron oxide coated mica, ethylene glycol mono-stearate, ethylene glycol distearate, polyethylene glycol distearate, bismuth oxychloride coated mica, myristyl myristate, guanine, glitter (polyester or metallic), and mixtures thereof. Other pearlescent materials can be found in U.S. Pat. Nos. 4,654,207 and 5,019,376, herein incorporated by reference. In an embodiment, the concentration of the opacifier, when present, ranges from about 0.01 wt % to about 5 wt %, by weight of the entire anti-dandruff hair care composition, or from about 0.1 wt % to about 3 wt %, or from about 0.1 wt % to about 2 wt %. Wt % is based on the weight of the entire composition.

5. Thickeners

Thickeners or rheology modifiers include, but are not limited to, acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate, and combinations thereof. In an embodiment, the concentration of the rheology modifier, when present, ranges from about 0.01 wt % to about 7 wt %, by weight of the entire anti-dandruff hair care composition, or from about 0.1 wt % to about 5 wt %, or from about 0.2 wt % to about 4 wt %. Wt % is based on the weight of the entire composition.

6. Buffers

The hair care compositions may have a pH ranging from about 3.0 to about 10, which may be stabilized by the presence of a buffer system. Suitable buffer solutions can be prepared using, for example, weak acid or weak base systems using citric acid, phosphoric acid, phthalic acid, glycine or mixtures thereof. In each case the proper buffering capacity is obtained by adjusting the final pH of the compositions to within the pH range indicated above. This may be done by using an acid (e.g., HCl, citric acid) or a base (e.g., NaOH, sodium citrate) as may be needed. The amount of buffer employed in the present compositions depends on the particular acid chosen but is generally from about 0.1 wt % to about 10 wt %, preferably from about 0.2 wt % to about 5 wt %. Wt % is based on the weight of the entire composition.

Additional agents, such as benefit agents, may also be included in the hair care compositions. The benefit agent may comprise a material selected from the group consisting of perfumes; brighteners; enzymes; sensates (cooling or warming); attractants, anti-bacterial agents; dyes; pigments; bleaches; and mixtures thereof. It should be further appreciated that the inventive combination of natural anti-dandruff actives disclosed herein may also be used in combination with secondary scalp benefit agents, such as soluble and/or insoluble anti-dandruff actives. Such anti-dandruff actives include but are not limited to azoles, such as ketoconazole, econazole, climbazole, and elubiol; keratolytic agents such as salicylic acid; and zinc-containing layered (ZLM) materials, pyridinethione anti-dandruff particulates such as zinc pyrithione, coal tar, sulfur, charcoal, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), Sensiva SC-50, Elestab HP-100, azelaic acid, lyticase, iodopropynyl butylcarbamate (IPBC), isothiazalinones such as octyl isothiazalinone, other natural oils, extracts, or compounds such as oil of bitter orange, tea tree oil, clove leaf oil, coriander, palmarosa, berberine, thyme red, cinnamon oil, cinnamic aldehyde, citronellic acid, hinokitol, ichthyol pale, and combinations thereof. In an embodiment, the concentration of the secondary scalp benefit agent ranges from about 0.01 wt % to about 5 wt %, by weight of the entire anti-dandruff hair care composition, or from about 0.1 wt % to about 3 wt %, or from about 0.1 wt % to about 2 wt %. Wt % is based on the weight of the entire composition. Alternatively, the inventive combination of natural anti-dandruff actives disclosed herein may also be void of any of the foregoing recited soluble and/or insoluble anti-dandruff actives.

The anti-dandruff hair care compositions are generally prepared by conventional methods known in the art shampoo compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. This optimization may include appropriate pH, and exclusion of materials that can complex or react with the active agent(s) and thus negatively impact stability or delivery.

The anti-dandruff hair composition may be in a single phase or a single product, or the anti-dandruff hair composition may be in a separate phases or separate products. If two products are used, the products may be used together, at the same time or sequentially. Sequential use may occur in a short time period, such as immediately after the use of one product, or it may occur over a period of hours or days.

Use of the Anti-dandruff Composition: According to yet another embodiment of the present invention, a method is provided for the treatment of a subject having dandruff and/or to prevent or inhibit the onset of dandruff symptoms associated with the proliferation of yeasts of the *Malassezia* genus on a scalp of a subject. The method includes contacting the subject's scalp or keratinous tissue with an effective quantity of the anti-dandruff composition of the present invention. The anti-dandruff composition may be massaged onto the scalp and should remain in contact with the subjects scalp or keratinous tissue for a duration of at least 15 seconds or more. Depending on the formulation, the anti-dandruff composition may be a leave in or it may be rinsed out.

Accordingly, in another embodiment, the method comprises topically applying an anti-dandruff composition comprising an effective amount of the anti-dandruff actives to a region of the subject's skin where inhibition of *Malassezia furfur* is needed or wanted, where the anti-dandruff actives remain in contact with the region for a duration of 15 seconds or more; and then rinsed out. In still another embodiment, the method comprises applying the composition according to a regimen, wherein said regimen comprises: (a) cleansing the scalp to form a cleansed scalp; (b) topically applying the anti-dandruff composition to said cleansed scalp.

The anti-dandruff composition may be used daily, weekly, or in a variety of regimens. The anti-dandruff composition may be used more than once a day, such as at night and in the morning. The product may be used after washing the hair (also on wet or dry hair), which may mean using the composition more than once per day on certain days or use only a few times per week. The anti-dandruff composition may be used three times per day, twice per day, once per day, six times per week, five times per week, four times per week, three times per week, two times per week, or one time per week. In some embodiments, the anti-dandruff composition is used four, five, six or seven times per week.

According to another embodiment, the anti-dandruff composition is applied to at least once a day for at least about four weeks, or at least twice a day for at least about four weeks. According to another embodiment, the anti-dandruff composition is applied at least once a day for at least about eight weeks. The anti-dandruff composition may be used by males and females.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Anti-Dandruff Actives

Extract of *Punica granatum*: 25 g of the flaked *Punica granatum* rind raw material (obtained from Pradip Agrotech Pvt Ltd.; Solapur, Maharashtra, India; phenolic content of 24.2 GAE/g) was extracted with 50% aqueous ethanol at 65° C. for 30 min and filtered to remove the undissolved solids from the filtrate. The undissolved solids were further extracted five more times with the same procedure as described above. The combined filtrates were filtered through a 10-13 micron filter cloth, evaporated in a rotary evaporator under vacuum to yield 13.98 g of dried solids having a phenolic content of 43.5 GAE/g (mass yield=55.92%). Based on LC/MS-QTOF analysis, this extract of *Punica granatum* contains gallic acid, punicalagin $\alpha$, punicalagin $\beta$, punicalin, ellagic acid hexoside, ellagic acid pentoside, ellagic acid deoxyhexoside, ellagic acid, and galloyl HHDP hexoside. HPLC quantification against standards provided 3.9 wt % ellagic acid, 0.5 wt % gallic acid, 0.22 wt % punicalagin B, and 0.05 wt % punicalagin A. This unstandardized product (PE 1) can be diluted with a sufficient quantity of glycerol, and then filtered through a 400 micron metal sieve, to form a standardized solution having 12% GAE (PE 2). Alternatively, subjecting fresh *Punica granatum* rind raw material to aqueous pressing and purification by column chromatography (DIAION™ HP20 resin, wash with water and elute with 50% aqueous ethanol), and spray drying yielded an unstandardized product with about 75 GAE and 30 wt % punicalagins, which was also dissolved in glycerol to form a standardized solution having 12% GAE (PE 3).

Essential oil of *Trachyspermum ammi*: The essential oil (EO) of Ajowan is produced by the steam distillation of ground, dried seeds of *Trachyspermum ammi* (obtained from Shree Agro International; Unja, Gujarat, India). The ground seeds are charged to the vessel and moistened before applying steam. Direct steam is applied, and the distillation continued for a minimum of about 15 hours to obtain a total yield of Ajowan EO in about 2 wt % to about 2.5 wt %, based on the dried weight of the Ajowan seeds (AJ 1). The EO product is a liquid and has pale yellow to brownish yellow color. It has the characteristic odor of cyminic, with a thymolic after note. Analysis by GC-MS using an Agilent 5977A, equipped with GC-7890B and 7693 auto sampler, operated in electron impact (EI) mode (70 ev) revealed that the major components of Ajowan EO are gamma-terpinene (45.7%), p-cymene (22.0%), and thymol (23.2%), where % is FID area % from the GC-MS analysis. Ajowan EO may be obtained from Kancor Ingredients LTD (Kerala, India).

Essential oil of *Mentha arvensis*: The essential oil (EO) of corn mint is produced by the steam distillation of the flowering herb of *Mentha arvensis*. The semi-dried corn mint leaves (obtained from Bareilly, Uttar Pradesh, India) are charged to a steam distillation vessel. Steam is slowly applied to distill out the EO and the process continued while monitoring the EO production. Average distillation time is approximately 5 to 7 hours, with a total yield of approximately 1.4 wt % to 1.6 wt %, based on the weight of the semi-dried corn mint leaves (CM 1). The corn mint EO product is a colorless or pale yellow liquid. Analysis by GC-MS revealed that the major constituent of corn mint essential oil is L-menthol (76.1%) and the other notable constituents include menthone (6.8%), isomenthone (3.6%), neomenthol (2.1%), menthyl acetate (2.1%), and limonene (1.7%), where % is FID area % from the GC-MS analysis. The corn mint EO may be obtained from Kancor Ingredients LTD (Kerala, India).

Combinations: Based on their additive and synergistic anti-dandruff activities (discussed below), blends or mixtures of the ingredients, along with optional carrier(s) and other functional ingredients may be advantageously pre-packaged and/or blended with a variety of hair care ingredients.

Antimicrobial Activity and Interaction Testing

Briefly, as is commonly known by those skilled in the art of the instant disclosure, assessment of *Malassezia furfur* inhibition may be accomplished following standard and accepted practices, such as that described in U.S. Patent Application Publication No. 2008/0249186. Accordingly, an external testing laboratory performed a series of against *Malassezia furfur* to evaluate antimicrobial activity and interactions (see Lens, et al. "Methods for the evaluation of antimicrobial activity of essential oils," J. Pharm. Belg. 1987). Inhibitory activity testing was conducted by mixing 100 μl of various dilutions of the test product at a double concentration with an equal volume (100 μl) of a double

TABLE 1

| | | | Control A | Ex. 1 B | Ex. 2 C | Ex. 3 D | Ex. 4 E |
|---|---|---|---|---|---|---|---|
| Part | Ingredient | Tradename | | | | | |
| A | Distilled water | n/a | 64.23 | 62.73 | 63.13 | 61.70 | 61.98 |
| A | ACRYLATES/C10-30 ALKYL ACRYLATE CROSSPOLYMER | CARBOPOL ® ETD 2020 | 0.20 | 0.2 | 0.2 | 0.19 | 0.19 |
| A | SODIUM HYDROXIDE 20% IN WATER | n/a | 0.10 | 0.1 | 0.1 | 0.09 | 0.09 |
| A | SODIUM LAURETH SULFATE AND WATER | TEXAPON ® N70 | 21.00 | 21.00 | 21.0 | 19.81 | 19.89 |
| A | COCAMIDE MIPA | COMPERLAN ® IP | 0.1 | 0.1 | 0.1 | 0.09 | 0.09 |
| A | GLYCOL DISTEARATE | TEGIN ® BL 315 | 2.00 | 2.00 | 2.00 | 1.89 | 1.89 |
| A | DISODIUM COCOAMPHODIACETATE | MIRANOL ® C2M CONC | 8.00 | 8.00 | 8.00 | 7.55 | 7.58 |
| A | DIMETHICONE | XIAMETER ® PMX-200 SILICONE FLUID 60000 CST | 2.50 | 2.50 | 2.50 | 2.36 | 2.37 |
| A | HYDROXYPROPYL GUAR & HYDROXYPROPYL GUAR - HYDROXYPROPYLTRIMONIUM CHLORIDE | JAGUAR ® C162 | 0 | 0 | 0 | 0.28 | 0.28 |
| A | GUAR - HYDROXYPROPYLTRIMONIUM CHLORIDE | JAGUAR ® C13S | 0.3 | 0.3 | 0.3 | 0 | 0 |
| A | PPG-5-CETETH-20 | PROCETYL ™ AWS | 0.3 | 0.3 | 0.3 | 0.28 | 0.28 |
| B | PE 2 | | 0 | 1.67 | 1.67 | 1.67 | 1.67 |
| B | CM 1 | | 0 | 1.0 | 0.5 | 1 | 0.5 |
| B | AJ 1 | | 0 | 0 | 0.1 | 0 | 0.1 |
| C | CITRIC ACID 20% IN WATER | N/A | 0.10 | 0.1 | 0.1 | 0.09 | 0.09 |
| C | PEG-32 | PLURACARE ® E 1500 | 0 | 0 | 0 | 3 | 3 |
| C | Glycerine | n/a | 1.17 | 0 | 0 | 0 | 0 |
| | | | 100 | 100 | 100 | 100 | 100 |

PE—pomegranate extract; AJ—ajowan essential oil; CM—corn mint essential oil; Part A—Shampoo chassis; Part B—anti-dandruff actives; Part C—pH or viscosity modifiers.

Preparation of the anti-dandruff shampoo begins with dispersing the CARBOPOL® in 40% of water and then neutralizing to pH=6 with sodium hydroxide. JAGUAR® C162 is dispersed in the remaining water and then added to the CARBOPOL® solution. After the addition of TEXAPON® N70, the mixture is heated to 70° C., the solid raw materials are added, i.e., COMPERLAN®, TEGIN® BL315. When the solids were well dissolved, the mixture was allowed to cool down, and the other ingredients (including the anti-dandruff actives PE 2, CM 1, and AJ 1) added and mixed well until complete homogeneity. pH was adjusted to 5.65 with citric acid and viscosity adjusted with PLURACARE® E1500.

strength Difco™ Sabouraud dextrose broth supplemented with olive oil, inoculated between 2 to 6×10⁵ cfu/mL. After incubation (24-72 hours, at 32.5° C.±2.5° C.), a spectrophotometric reading at 620 nm is performed and the percentage of growth calculated from optical density (OD) measuring each concentration with respect to a positive growth control according to the following equation:

$$\% \text{ of growth} = [(OD_{product} - OD_{absorbance-control})]/(OD_{positive\ growth-control}).$$

Each concentration was tested in triplicate, and two assays were performed per product. The positive growth control consisted of 100 μl 1% agar solution mixed with 100 μl of inoculated broth.

TABLE 2

| Minimum Inhibitory Concentrations against *M. furfur*. | | | | |
|---|---|---|---|---|
| Sample | Comment | Test 1 | Test 2 | *M. furfur* strain |
| PE 1 | MICRA 150624 | 0.1% | 0.1% | CIP 1634.84 |
| PE 2 | MICRA-L 170105 | 0.1% | 0.1% | CIP 1634.84 |
| PE 3 | MICRA-P | 0.05% | 0.05% | CBS 1878 |
| CM 1 | OMAO 2006501 | 0.5% | 0.5% | CIP 1634.84 |
| CM 1 | OMAO 2006501 | 1% | 1% | CBS 1878 |
| AJ 1 | AJTEO 204829 | 1% | 1% | CIP 1634.84 |
| AJ 1 | AJTEO 204829 | 0.5% | 0.5% | CBS 1878 |
| PU | Punicalagins A&B | 0.05% | 0.05% | CBS 1878 |
| EA | Ellagic Acid | 0.5% | 0.5% | CBS 1878 |
| Shampoo A | Control, Table 1 | 10% | — | CIP 1634.84 |
| Shampoo B | Example 1, Table 1 | ≤5% | ≤1% | CIP 1634.84 |
| Shampoo C | Example 2, Table 1 | ≤5% | ≤1% | CIP 1634.84 |
| Shampoo F | Comparative | ≤5% | — | CIP 1634.84 |

PE—pomegranate extract; AJ—ajowan essential oil; CM—corn mint essential oil; PU—punicalagins A&B; EA—ellagic acid; Comparative Shampoo F = HEAD & SHOULDERS ®, Procter & Gamble, UK.; Classic, Lot. No. (L) 60435395KF.

Inhibition studies revealed that the shampoo formulations including a plurality of the nature-derived anti-dandruff actives of the present invention (i.e., Shampoos B and C) possessed enhance activity over the control (Shampoo A), and were approximately as effective as the comparative Shampoo F, which utilizes synthetic zinc pyrithione.

Study of Associations. After obtaining the MIC levels for each of the anti-dandruff actives by broth dilution method, a checkerboard titration technique was performed to assess the synergistic activity of the combinations. In order to evaluate the activity of the combinations of the anti-dandruff actives, a Fractional Inhibitory Concentration index ($FIC_{index}$) was calculated: ($FIC_{index}$)=$FIC^A$+$FIC^B$, where $FIC^A$ and $FIC^B$ represent the minimum concentrations inhibiting the *M. furfur* growth for anti-dandruff actives A and B, respectively. And $FIC^A$=$MIC^A_{combination}$/$MIC^A_{alone}$, and $FIC^B$=$MIC^B_{combination}$/$MIC^B_{alone}$.] A mean FIC index was calculated based on the following equation: $FIC_{index}$=$FIC^A$+$FIC^B$. Synergism is defined as FIC≤0.75; additive as FIC ~1; indifference as 1<FIC<2; and antagonism is defined as FIC>2, as reported by J. L. Pons; N. Bonnaveiro; J. Chevalier; and A. Crémieux, "Evaluation of antimicrobial interactions between chlorhexidine, quaternary ammonium compounds, preservatives and excipients," J. Appl. Bacteriology, 1992, 73(5), 395-400.

The association testing of the nature-derived anti-dandruff actives of the present invention utilizing the checkerboard titration technique revealed the synergistic activity of the combinations of a) the punicalagin composition (PE 2) and the first monoterpenoid composition (AJ 1); b) the second monoterpenoid composition (CM1) and the first monoterpenoid composition (AJ 1); and the first monoterpenoid composition (AJ 1) and punicalagins A & B (PU). The combination of the punicalagin composition (PE 1) and the second monoterpenoid composition (CM 1) was shown to be additive, whereas the combination of the first monoterpenoid composition (AJ 1) and ellagic acid (EA) was shown to be indifferent.

The association testing of the major components of the first monoterpenoid composition (i.e., thymol (TML), gamma-terpinene (GTP), and para-cymene (PCY) and the pomegranate extract having a punicalagins content of about 30 wt % on a dry weight basis (PE 3) revealed that the bi-component mixture of PE 3 and para-cymene (PCY) demonstrated synergistic activities against *Malassezia furfur*. The bi-component mixture of the punicalagin composition having a punicalagins content of at least 30 wt % on a dry weight basis (PE 3) and the second monoterpenoid composition (CM 1) was shown to be synergistic against *Malassezia furfur*.

Clinical Study

Protocol: Over 80 prescreened subjects having dandruff symptoms participated in a 28 day blind study, prior to which subjects completed a 14-day wash-out period consisting of a daily wash using a neutral shampoo (Szampon Familijny®, Pollena-Savona Sp. z o. o.; Batches 170270, 160492). In the study, inventive Shampoo D (Table 1, Example 3; combination of pomegranate extract and corn mint EO) and inventive Shampoo E (Table 1, Example 4; combination of pomegranate extract, corn mint EO, and ajowan EO) were tested against comparative Shampoo F (HEAD & SHOULDERS®, Procter & Gamble, UK; Classic, Lot. No. (L) 60435395KF, zinc pyrithione active). Prior to and after adhering to the required 28 day protocol, each scalp of each subject was assessed for adherent and non-

TABLE 3

| Association testing of anti-dandruff active combinations. | | | | | | | | |
|---|---|---|---|---|---|---|---|---|
| Samples | | | MIC A | MIC B | MIC in the associations | | FIC | |
| A | B | *M. furfur* strain | Alone % | Alone % | A % | B % | Index | Conclusion |
| PE 2 | AJ 1 | CIP 1634.84 | 0.2 | 1 | 0.025 | 0.5 | 0.63 | Synergistic |
| PE 1 | CM 1 | CIP 1634.84 | 0.2 | 0.5 | 0.1 | 0.25 | 1.00 | Additive |
| CM 1 | AJ 1 | CIP 1634.84 | 0.5 | 1 | 0.0625 | 0.5 | 0.63 | Synergistic |
| AJ 1 | PU | CBS 1878 | 0.25 | 0.05 | 0.0625 | 0.0125 | 0.5 | Synergistic |
| AJ 1 | EA | CBS 1878 | 0.25 | 0.5 | 0.25 | 0.25 | 1.5 | Indifferent |
| PE 3 | AJ 1 | CBS 1878 | 0.05 | 0.25 | 0.0125 | 0.125 | 0.75 | Synergistic |
| PE 3 | CM 1 | CBS 1878 | 0.05 | 1 | 0.0125 | 0.25 | 0.5 | Synergistic |
| PE 3 | TML | CBS 1878 | 0.05 | 0.05 | 0.0125 | 0.05 | 1.25 | Indifferent |
| PE 3 | GTP | CBS 1878 | 0.05 | >1 | 0.05 | 0.125 | 1.13 | Indifferent |
| PE 3 | PCY | CBS 1878 | 0.1 | 0.5 | 0.0125 | 0.25 | 0.625 | Synergistic |

PE—pomegranate extract; AJ—ajowan essential oil; CM—corn mint essential oil; TML—thymol; GTP—gamma-terpinene; PCY—para-cymene adherent dandruff and given a score based on the qualitative dandruff criteria provided in Table 4.

TABLE 4

Qualitative Dandruff Scoring.

| Score | Non-adherent dandruff | Adherent dandruff |
|---|---|---|
| 0 | No dandruff | No squamae |
| 1 | A few dispersed dandruff flakes | A few dispersed squamae flakes |
| 2 | A small quantity of dandruff flakes | A small quantity of squamae dandruff |
| 3 | A moderate quantity of dandruff flakes | A moderate quantity of squamae dandruff |
| 4 | A large quantity of dandruff | A large quantity of dandruff |
| 5 | A very large quantity of dandruff flakes | A very large quantity of squamae over the whole scalp |

The clinical "total dandruff score" is the sum of the adherent and non-adherent dandruff.

TABLE 5

Total Dandruff Scoring Results.

| Sample | Non-adherent score | Adherent score | Total |
|---|---|---|---|
| Shampoo D | −1.23 | −0.86 | −2.09 |
| Shampoo E | −1.01 | −0.87 | −1.87 |
| Shampoo F | −1.77 | −1.37 | −3.13 |

After following the prescribed 28 day testing protocol, all the test products (Shampoos D-F) were very well tolerated on the cutaneous level, and demonstrated significant decrease in adherent, non-adherent, and total dandruff score (see Table 5). The inventive shampoos (Shampoo D and E), which utilize nature-based, naturally-derived anti-dandruff actives, were shown to be effective at treating dandruff without using the synthetic zinc pyrithione anti-dandruff active (which is used in comparative Shampoo F).

Although not wishing to be limited by any particular theory, it is believed that topical application of the anti-dandruff actives in a dermatologically-acceptable carrier decreases the physical signs of dandruff by inhibiting the proliferation of *Malassezia furfur*. Accordingly, topical application of the anti-dandruff compositions may be used to treat dandruff or used prophylactically to inhibit the onset of dandruff caused by the proliferation of *Malassezia furfur*.

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "25° C." is intended to mean "about 25° C."

While the present invention is illustrated by the description of one or more embodiments thereof, and while embodiments have been described in considerable detail, they are not intended to restrict or in any way limit the scope of the appended claims to such detail. Additional advantages and modification will readily appear to those skilled in the art.

The invention in its broader aspects is therefore not limited to the specific details, representative product and method, and illustrative examples shown and described. Accordingly, departures from such details may be made without departing from the scope of the general inventive concept embraced by the following claims.

What is claimed is:

1. An anti-dandruff composition comprising:
   a combination of anti-dandruff actives, said anti-dandruff actives comprising:
      a punicalagin composition derived from extracting pomegranate rind with an aqueous extraction liquid comprising water or an aqueous alcoholic solution, wherein the punicalagin composition comprises a polyphenol content of at least 30 gallic acid equivalents (GAE) on a dry weight basis, and wherein the punicalagin composition comprises punicalagin A, punicalagin B, or both in 0.1 wt % or more based on a dry weight basis;
      a first monoterpenoid composition comprising an ajowan essential oil comprising p-cymene, thymol, and gamma-terpinene;
      a second monoterpenoid composition comprising a corn mint essential oil comprising menthol, menthone, isomenthone, menthyl acetate, neomenthol, and limonene; and
   a dermatologically-acceptable carrier,
   wherein said anti-dandruff actives are present in the anti-dandruff composition in an amount effective to treat dandruff.

2. The anti-dandruff composition of claim 1, wherein the punicalagin composition comprises less than 5 wt % ellagic acid based on a dry weight basis.

3. The anti-dandruff composition of claim 1, wherein the first monoterpenoid composition is present in an amount in a range from 0.1 wt % to 5 wt % based on the entire weight of the anti-dandruff composition.

4. The anti-dandruff composition of claim 1, wherein the punicalagin composition is present in an amount in a range from 0.1 wt % to 10 wt % based on the total weight of the anti-dandruff composition.

5. The anti-dandruff composition of claim 1, wherein the second monoterpenoid composition is present in an amount in a range from 0.25 wt % to 10 wt % based on the total weight of the anti-dandruff composition.

6. The anti-dandruff composition of claim 1,
   wherein the punicalagin composition is present in an amount in a range from 0.1 wt % to 10 wt %;
   wherein the first monoterpenoid composition is present in an amount in a range from 0.1 wt % to 5 wt %;
   wherein the second monoterpenoid composition is present in an amount in a range from 0.25 wt % to 10 wt %;
   wherein the dermatologically-acceptable carrier comprises water and a detersive surfactant; and
   wherein the wt % is based on the total weight of the anti-dandruff composition.

7. The anti-dandruff composition of claim 6, wherein the dermatologically-acceptable carrier comprising water and the detersive surfactant is present in a range from about 30 wt % to about 99 wt % based on the total weight of the anti-dandruff composition.

8. A method of treating a subject having dandruff or inhibiting an onset of dandruff symptoms associated with the proliferation of yeasts of the *Malassezia* genus on a scalp of a subject said method comprising:

contacting the subject's scalp or keratinous tissue with an effective amount of the anti-dandruff composition of claim 1.

9. The method of claim 8, further comprising massaging the anti-dandruff composition onto the subject's scalp or keratinous tissue and maintaining the anti-dandruff composition in contact with the subject's scalp or keratinous tissue for a duration of at least 15 seconds.

10. The method of claim 9, further comprising rinsing out the anti-dandruff composition after the anti-dandruff composition has been massaged onto the scalp or keratinous tissue.

11. The method of claim 8, wherein the punicalagin composition is present in the anti-dandruff composition in an amount in a range from 0.1 wt % to 10 wt %;

wherein the first monoterpenoid composition is present in an amount in a range from 0.1 wt % to 5 wt %;

wherein the second monoterpenoid composition is present in an amount in a range from 0.25 wt % to 10 wt %;

wherein the dermatologically-acceptable carrier comprises water and a detersive surfactant; and wherein the wt % is based on the total weight of the anti-dandruff composition.

12. The method of claim 11, wherein the punicalagin composition comprises less than 5 wt % ellagic acid based on a dry weight basis.

\* \* \* \* \*